United States Patent [19]

Stossel et al.

[11] Patent Number: 5,464,817
[45] Date of Patent: Nov. 7, 1995

[54] METHOD FOR REDUCING THE VISCOSITY OF PATHOLOGICAL MUCOID AIRWAY CONTENTS IN THE RESPIRATORY TRACT COMPRISING ADMINISTERING ACTIN-BINDING COMPOUNDS WITH OR WITHOUT DNASE I

[75] Inventors: Thomas P. Stossel, Belmont; Stuart E. Lind, Wellesley; Paul A. Janmey, Arlington, all of Mass.

[73] Assignee: Brigham and Women's Hospital, Boston, Mass.

[21] Appl. No.: 42,247

[22] Filed: Apr. 2, 1993

Related U.S. Application Data

[63] Continuation-in-part of Ser. No. 774,738, Oct. 10, 1991, Pat. No. 5,260,224, which is a continuation of Ser. No. 507,214, Apr. 11, 1990, abandoned.

[51] Int. Cl.$^6$ ............................ C12N 9/00; C07K 14/00; C07K 7/00
[52] U.S. Cl. .................... 514/2; 514/12; 514/851; 514/826; 514/958; 424/94.1; 530/350; 530/324; 530/325; 530/326; 530/327; 530/328; 530/329; 530/330; 435/68.1; 435/183
[58] Field of Search ................................ 514/2, 12, 851, 514/826, 958; 435/68.1, 183; 424/94.1; 530/350, 324, 325, 326, 327, 328, 329, 330

[56] References Cited

FOREIGN PATENT DOCUMENTS

| 0526544 | 12/1992 | European Pat. Off. |
| WO91/15770 | 10/1991 | WIPO. |
| WO94/04704 | 3/1994 | WIPO. |

OTHER PUBLICATIONS

Hubbard et al. 1992 New Engl. J. Med. 326:812–815.
Way et al. 1988 J. Mol. Biol. 203: 1127–1133.
Vasconcellos et al. 1994 Science 263:969–971.
Lieberman 1968 JAMA 205:114–115.
Smith et al. 1985 Clinical Research 33: 472A.
Van Vaelen et al. 1980 J. Biol. Chem. 255:2270–2272.
Chaponnier et al. 1986 J. Cell Biol. 103:1473–1481.
Aitken et al., Recombinant human DNase inhalation in normal subjects and patients with cystic fibrosis, JAMA 267:1947–1951 (1992).
André et al., Severin, gelsolin, and villin share a homologous sequence in regions presumed to contain F–actin severing domains, J. Biol. Chem. 263:722–727 (1988).
Bryan, Gelsolin h as three actin–binding sites, J. Cell Biol. 106:1553–1562 (1988).
Chaponnier et al., Reversibility of gelsolin/actin interaction in macrophages, J. Exp. Med. 165:97–106 (1987).
Cooke et al., Serum vitamin D–binding protein is a third member of the albumin and alpha fetoprotein gene family, J. Clin. Invest. 76:2420–2424 (1985).
Cooper et al., Microinjection of gelsolin into living cells, J. Cell Biol. 104:491–501 (1987).
Coué et al., Effects of serum vitamin–D–binding protein on actin in the presence of the plasma gelsolin, Eur. J. Biochem. 160:273–277 (1986).
Goldschmidt–Clermont et al., Proportion of circulating Gc (vitamin D–binding protein) in complexed form: relation to clinical outcome in fulminant hepatic necrosis, Gastroenterology 94:1454–1458 (1988).
Haddad et al., Angiopathic consequences of saturating the plasma scavenger system for actin, Proc. Natl. Acad. Sci. USA 87:1381–1385 (1990).
Harper et al., G–actin infusions: plasma vitamin D binding protein protects against endothelial damage and intra–vascular filament formation, Clin. Res. 36:625A (1988).
Janmey, Mechanical properties of cytoskeletal polymers, Curr. Opin. Cell Biol. 2:4–11 (1991).
Janmey et al., Effects of semi–dilute actin solutions on the mobility of fibrin protofibrils during clot formation, Biochim. Biophys. Acta 841:151–158 (1985).
Janmey et al., Capacity of human serum to depolymerize actin filaments, Blood 70:524–530 (1987).
Janmey et al., Modulation of gelsolin function by phospatidylinositol–4,5–biphosphate, Nature 325: 362–364 (1987).
Janmey et al., Polyphosphonositide micelles and polyphosphoinositide–containing vesicles dissociate endogenous gelsolin–actin complexes and promote actin assembly from the fast–growing end of actin filaments blocked by gelsolin, J. Biol. Chem. 262:12228–12236 (1987).
Janmey et al., Viscoelasticity of F–actin and F–actin/gelsolin complexes, Biochem. 27:8218–8227 (1988).
Janmey et al., Effects of actin filaments on fibrin clot structure and lysis, Blood 80:928–936 (1992).
Kwiatkowski et al., Isolation and properties of two actin–binding domains in gelsolin, J. Biol. Chem. 260:15232–15238 (1985).
Kwiatkowski et al., Plasma and cytoplasmic gelsolins are encoded by a single gene and contain a duplicated actin–binding domain, Nature 323:455–458 (1986).
Kwiatkowski et al., Muscle is the major source of plasma gelsolin, J. Biol. Chem. 263:8239–8243 (1988).

(List continued on next page.)

Primary Examiner—Garnette D. Draper
Assistant Examiner—Elizabeth C. Kemmerer
Attorney, Agent, or Firm—Fish & Neave; James F. Haley, Jr.; Jane T. Gunnison

[57] ABSTRACT

The invention is generally directed to methods of promoting normal respiratory tract airflow in subjects with restricted airflow and ciliary clearance caused by the presence of pathological airway contents, and particularly mucoid contents. Actin-binding proteins are administered into the respiratory tract of a subject with a pathological respiratory condition involving the presence of such contents. The actin-binding protein binds to actin polymers in the contents and decreases the viscosity. The actin binding proteins also prevent actin from binding to exogenous or endogenous DNase, thus increasing the degradation of DNA polymers in the contents.

16 Claims, 2 Drawing Sheets

OTHER PUBLICATIONS

Kwiatkowski et al., Genomic organization and biosynthesis of secreted and cytoplasmic forms of gelsolin, *J. Cell Biol.* 106:375–384 (1988).

Kwiatkowski et al., Identification of critical functional and regulatory domains in gelsolin, *J. Cell Biol.* 108:1717–1726 (1989).

Lazarides et al., Actin is the naturally occurring inhibitor of deoxyribonuclease I, *Proc. Natl. Acad. Sci. USA* 71:4742–4746 (1974).

Lind et al., Human plasma gelsolin binds to fibronectin, *J. Biol. Chem.* 259:13262–13266 (1984).

Lind et al., Role of plasma gelsolin and the vitamin D-binding protein in clearing actin from the circulation, *J. Clin. Invest.* 78:736–742 (1986).

Lind et al., Depression of gelsolin levels and detection of gelsolin-actin complexes in plasma of patients with acute lung injury, *Am. Rev. Respir. Dis.* 138:429–434 (1988).

Matsudaira et al., Pieces in the actin-severing protein puzzle, *Cell* 54:139–140 (1988).

Peitsch et al., Characterization of the endogenous deoxyribunuclease involved in nuclear DNA degradation during apoptosis (programmed cell death), *The EMBO Journal* 12:371–377 (1993).

Pollard et al., Actin and actin-binding proteins. A critical evaluation of mechanisms and functions, *Ann. Rev. Biochem.* 55:987–1035 (1986).

Scarborouugh et al., Aggregation of platelets by muscle actin. A multivalent interaction model of platelet aggregation by ADP, *Biochem. Biophys. Res. Commun.* 100:1314–1319 (1981).

Shak et al., Recombinant human DNase I reduces the viscosity of cystic fibrosis sputum, *Proc. natl. Acad. Sci. USA* 87:9188–9192 (1990).

Smith et al., Circulating actin-gelsolin complexes following oleic acid-induced lung injury, *Am. J. Path.* 130:261–267 (1988).

Smith et al., Decreased plasma gelsolin levels in patients with *Plasmodium falciparum* malaria: a consequence of hemolysis?, *Blood* 72:214–218 (1988).

Stossel et al., Nonmuscle actin-binding proteins, *Ann. Rev. Cell Biol.* 1:353–402 (1985).

Stossel, The actin system and the rheology of peripheral cytoplasma, *Biorheology* 23:621–631 (1986).

Way et al., Expression of human plasma gelsolin in *Escherichia coli* and dissection of actin binding sites by segmental deletion mutagensis, *J. Cell Biol.* 109:593–605 (1989).

Yang et al., Human group-specific component (Gc) is a member of the albumin family, *Proc. Natl. Acad. Sci. USA* 82:7994–7998 (1985).

Yin et al., Actin filament servering by gelsolin, *J. Cell Biol.* 107:465a (1988).

Yin et al., Identification of a polyphosphoinositide-modulated domain in gelsolin which binds to the sides of actin filaments, *J. Cell Biol.* 106:805–812 (1988).

Young et al., Correlation between extent of liver damage in fulminant hepatic necrosis and complexing of circulating group-specific component . . . , *J. Lab. Clin. Med.* 110:83–90 (1987).

METHOD FOR REDUCING THE VISCOSITY OF PATHOLOGICAL MUCOID AIRWAY CONTENTS IN THE RESPIRATORY TRACT COMPRISING ADMINISTERING ACTIN-BINDING COMPOUNDS WITH OR WITHOUT DNASE I

This invention was supported by United States Federal Government funding. The government has certain rights in this invention. This application is a continuation-in-part of application Ser. No. 07/774,738, filed Oct. 10, 1991 and issued on Nov. 9, 1993, as U.S. Pat. No. 5,260,224, which is a continuation of application Ser. No. 07/507,214, filed Apr. 11, 1990, now abandoned.

FIELD OF THE INVENTION

The present invention relates to the treatment of respiratory disorders in which it is desired to disaggregate, depolymerize, or solubilize actin filaments or to promote the degradation of DNA in respiratory tract mucus. The invention particularly relates to solubilization and increased clearance of mucus obstructing the respiratory tract in airway diseases. The invention relates to a method for reducing the viscosity of mucus by instillation of actin-binding proteins into the respiratory tract. The invention also relates to a method for facilitating the action of DNase I in respiratory tract treatments by blocking actin binding to DNase I or reducing the levels of actin in respiratory tract mucus. The method involves the administration of efficacious amounts of actin-binding compounds, or actin-binding fragments thereof, such that the compounds or fragments are active in the respiratory tract of a subject in need of such treatment.

BACKGROUND OF THE INVENTION

Airway Obstruction

Airway obstruction caused by inflammatory exudation is a major cause of morbidity and mortality. Mucus plugging and stasis is a feature of chronic bronchitis, asthmatic bronchitis, bacterial bronchopneumonia and, especially, cystic fibrosis, and is associated with destruction of lung substance. Mucus also contributes to the morbidity of acute and chronic sinusitis and even the common cold.

Mucoid obstruction of the respiratory system is multifactorial. One factor is increased mucus synthesis and release caused by inflammatory mediators elicited by infection or irritation. In cystic fibrosis, the viscosity of mucus is increased, presumably because of abnormal epithelial ion transport which affects the hydration or charge of the ionic polymers composing the mucus substance. The thick mucus of cystic fibrosis prevents bacterial clearance by ciliary transport and favors the growth of bacteria, especially Pseudomonas aeruginosa. These bacteria or irritants, such as tobacco smoke generate chemoattractants which recruit leukocytes into the airway. As the leukocytes engage bacteria they degenerate, and their components contribute debris that affect the viscoelasticity of the airway contents.

Much research in the area of pathological mucoid airway contents has focused on DNA, since DNA was originally isolated from pus. However, there has also been research on the mucopolysaccharide composition of mucus and the role of disulfide bonding (Roberts, G. P., *Arch. Biochem. Biophys.* 173:528–537 (1976); Roberts, G. P., *Eur. J. Biochem.* 50:265–280 (1974); Charman, J., et al., *Brit. J. Dis. Chest* 68:215 (1974); Bhaskar, K. R., et al., *Exp. Lung Res.* 10:401–422 (1986); Lethem, M. I., et al., *Eur. Respir. J.* 3:19–23 (1990)). Purulent mucus contains about 10–13 mg/ml of DNA, an ionic polymer predicted to affect the rheologic properties of airway fluids. Accordingly, bovine pancreatic DNase I, an enzyme that degrades DNA, was tested as a mucolytic agent many years ago but did not enter clinical practice, because of side effects induced by antigenicity and/or contaminating proteases. Recently, recombinant human DNase I was tested as a therapeutic agent. The cDNA for human. DNase I was cloned and expressed. It was shown to diminish the viscosity of cystic fibrosis mucus in vitro (Shak, S., et at., *Proc. Natl. Acad. Sci. USA* 87:9188–9192 (1990)). Human DNase I has moved beyond phase I trials and reportedly is effective in improving subjective and possibly objective manifestations of purulent airway disease (Aitken, M., et al., *JAMA* 267:1947–1951 (1992)).

Extracellular Actin

Actin is the most abundant protein in nucleated animal cells and constitutes 10–20% of the protein of many nucleated cells and 30% of the protein of muscle cells. Actin molecules each bind an ATP or ADP molecule and self-assemble into long filaments during which the ATP is hydrolyzed into ADP.

Injury to animal tissues results in the release of actin into the extracellular space. Although approximately half of nonmuscle cell actin is F-actin, (the double-helical, rodlike, filament form of actin which is assembled from G-actin monomers), the ionic conditions of extracellular fluids favor actin polymerization, so that virtually all the actin released from dying cells would be expected to polymerize into filaments if sufficiently concentrated (greater than a few micrograms per milliliter) (Lind, S. E. et al., *Am. Rev. Respir. Dis.* 138:429–434 (1988)). Actin polymerizes into long, rod-like filaments which are relatively resistant to degradation by proteolytic enzymes. In purified solutions, in the absence of filament-shortening proteins, actin filaments can easily attain lengths of several microns.

Because of the large amounts of actin in cells, the release of actin from dying cells provides sufficient actin to have a significant affect on the microenvironment, either by increasing the viscosity of extracellular fluids, such as mucin, and/or by entrapping cells or by other, as yet unidentified toxic effects. Infusion of extracellular free actin is toxic to animal tissues (Harper, K. D. et al., *Clin. Res.* 36:625A (1988); Haddad, J. G. et al., *Proc. Natl. Acad. Sci. USA* 87:1381–1385 (1990)). If actin released from injured cells were to be bound to an intracellular actin-binding protein, such as those discussed below, this actin would remain monomeric or oligomeric.

Actin-Binding Proteins

There are many proteins which naturally associate with actin. For a review of actin-binding proteins, see Stossel, T. P. et al., *Ann. Rev. Cell Biol.* 1:353–402 (1985); Pollard, T. D. et al., *Ann. Rev. Biochem.* 55:987–1035 (1986). However, two proteins, gelsolin and DBP (vitamin D binding protein) are thought to be primarily responsible for binding extracellular actin (Janmey, P. A. et al., *Blood* 70:529–530 (1987)).

Plasma gelsolin (sometimes called brevin) and DBP (also called Gc globulin) are the two high affinity actin-binding proteins that exist in plasma. High affinity actin-binding proteins bind actin with a $K_d$ of less than $10^{-8}$. Both gelsolin and DBP bind to actin in blood serum and have actin depolymerizing activity. DBP preferentially binds monomeric actin while gelsolin preferentially binds actin filaments.

Gelsolin is a multifunctional actin-binding protein obtained from mammalian cytoplasm and extracellular fluids. Plasma gelsolin differs from cellular gelsolin by an additional 25 amino acids at the amino terminus of the molecule. Both gelsolins are the products of a single gene. Plasma gelsolin has three actin-binding sites and binds with high affinity to either G-actin or F-actin.

Plasma gelsolin binds a second actin molecule with a higher affinity than it binds a first actin molecule. Thus, it preferentially forms 2:1 complexes over 1:1 complexes and binds filaments in preference to monomers. When added to F-actin, plasma gelsolin severs the filament in a nonproteolytic manner and remains bound to one end of the newly formed filament. If free gelsolin molecules are present, they will sever the actin filament successively until only 2:1 actin-gelsolin complexes are present, thereby rapidly depolymerizing the filament.

Free and complexed (to actin) gelsolin molecules differ in their functional properties. Although free gelsolin can sever actin filaments, actin-gelsolin complexes cannot.

Gelsolin's primary function in the plasma and other extracellular fluids is to sever actin filaments. If gelsolin is present in excess of actin, only gelsolin-actin complexes result; if actin is in excess, there are free actin oligomers and gelsolin-actin complexes. The actin severing occurs by way of a nonproteolytic cleavage of the noncovalent bond between adjacent actin molecules. Gelsolin's severing activity is activated by micromolar $Ca^{++}$ and by pH above 6, and has been shown to be inhibited by phosphatidyl inositol 4-5-bisphosphate ($PIP_2$) and phosphatidyl inositol-4-monophosphate (PIP). Since extracellular $Ca^{++}$ concentrations are at millimolar levels and extracellular fluids do not normally contain PIP or $PIP_2$ in a form that inhibits gelsolin, plasma gelsolin is constitutively active in extracellular fluids.

Human extracellular (plasma) gelsolin cDNA has been cloned and sequenced (Kwiatkowski, D. J. et al., *Nature* 323:455–458 (1986); Kwiatkowski, D. J. et al., *J. Cell Biol.* 106:375–384 (1988)). Fragments of the native protein which retain the ability to bind actin have been identified (Bryan, J., *J. Cell Biol.* 106:1553–1562 (1988); Yin, H. L. et al., *J. Cell Biol.* 107: 465a (1988), abst. no. 2616); Kwiatkowski, D. J. et al., *J. Cell Biol.* 108:1717–1726 (1989); Way, M. et al., *J. Cell Biol.* 109:593–605 (1989)). There is no evidence to suggest that it is genetically polymorphic (except in the uncommon genetic disorder called Finnish-type amyloidosis in which single amino acid mutations are found in plasma gelsolins), indicating that use of recombinant human protein should not lead to immunogenic or other toxic effects. Plasma gelsolin has been detected in many body fluids, suggesting that gelsolin may be a normal component of airway fluid, at least in states of inflammation.

DBP has also been cloned (Cooke, N. E. et al., *J. Gin. Invest.* 76:2420–2424 (1985); Yang, F. et al., *Proc. Natl. Acad. Sci. USA* 82:7994–7998 (1985)). DBP has a single actin binding site and binds constitutively to monomeric but not F-actin.

Actin and DNase I

The catalytic activity of DNase I is inhibited by actin, to which the enzyme binds tightly (Lindberg, U., *Biochem. Biophys. Acta* 82:237–248 (1964); Lazarides and Lindberg, *Proc. Natl. Acad. Sci. USA* 71:4742–4746 (1974)). In addition, DNase I, by ligating actin subunits, can depolymerize actin filaments. This background suggested that DNase I may, in addition to degrading DNA, depolymerize actin in airway secretions.

Actin comprises about 10% of the protein mass of leukocytes. It follows, therefore, that abundant actin, as well as DNA polymers, might exist in purulent airway contents. If actin does exist in these contents, the efficacy of DNase I in DNA degradation would predictably be reduced by binding to actin present in the very secretions for which DNase I was intended.

Actin filaments alone produce networks of high elasticity, and when interpenetrated within mucus and/or DNA polymers, predictably would contribute to very rigid gels as they do with fibrin (Janmey, P. A., *Blood* 80:928–936 (1992)). Introduction of actin-binding molecules that disaggregate actin filaments, especially by severing actin filaments (Janmey, P. A., *Curr. Opinion Cell Biology* 3:4–11 (1991)) is therefore an attractive approach to reducing the consistency of airway mucus, and especially purulent airway mucus.

Since actin inhibits the catalytic activity of DNase I, actin-binding molecules should also enhance the efficacy of DNase I in degrading DNA by solubilizing actin and facilitating its removal from DNA-containing airway mucus in which DNase I is intended to be effective.

Summary of the Invention

The present invention is based upon the Applicants' consideration that, since leukocytes are a significant component of purulent mucus and actin comprises about 10% of the protein mass of leukocytes, abundant actin might exist in purulent mucoid airway contents. The invention is also based on the consideration that the efficacy of DNase I in degrading the DNA polymers in purulent mucus would predictably be reduced by binding to actin present in the mucus. Therefore, the effect of both endogenous DNase I and DNase I added for therapeutic purposes would be reduced by binding to actin present in the very secretions for which the enzymes were intended.

Accordingly, the present invention is based upon the Applicant's consideration that the administration of actin-binding compounds, or biologically active derivatives thereof, to subjects with pathological mucoid airway contents will provide treatment of and protection against obstruction of the respiratory tract. It is therefore an object of the invention to provide a method for depolymerizing actin filaments, preventing actin polymerization, and for decreasing the levels of actin in the respiratory tract of individuals with airway disease.

It is an object of the invention to provide a method for the reduction of viscosity or solubilization of mucoid airway contents, obstructing the normal patency and flow of air in the respiratory tract in individuals with airway disease, and especially inflammatory airway disease.

Accordingly, the invention provides a method to reduce the viscosity or consistency of pathological airway contents by instillation into the respiratory tract of actin-binding compounds, and especially actin-binding proteins which: 1) disaggregate (depolymerize, fragment and dissociate) actin filaments released from disrupted leukocytes and other cells that solidify airway contents, and especially mucoid airway contents, and/or 2) prevent actin from inhibiting the action of the enzyme DNase I which degrades DNA polymers that increase the viscoelasticity of mucus. The DNase I may be endogenous or supplied for therapeutic purposes by aerosolization or any other appropriate and effective means.

Accordingly, a further object of the invention is reducing the level of actin binding to DNase I in the respiratory tract by the administration of actin binding compounds, and especially actin-binding proteins, to the respiratory tract. A further object of the invention is to enhance DNA degradation in pathological mucoid airway contents by the administration of actin binding compounds, and especially actin-binding proteins.

These and other objects of the invention, which will hereinafter become more readily apparent, have been obtained by administering to subjects with mucoid airway contents causing airway obstruction, one or more actin-binding proteins or active fragments thereof, in doses and under a regimen that treat the obstruction which occurs after actin and/or DNA release into said contents.

BRIEF DESCRIPTION OF THE FIGURES

FIG. 1 Dynamic shear moduli of cystic fibrosis sputum. Sputum samples with or without gelsolin or gelsolin fragment were placed between the parallel circular plates of a torsion pendulum (Ferry, J. D. *Viscoelastic Properties of Polymers*, 3rd Ed., John Wiley & Sons, New York (1980)) and a momentary displacement was applied to the arm attached to the upper sample plate. The dynamic shear modulus, G', was calculated from the frequency and damping of the resulting free oscillations. G' of actin polymer-containing solutions depends strongly on the average actin filament length (Janmey et al., *Biochemistry* 27:8218–8226 (1988)). 1A: Cystic fibrosis sputum alone; 1B: Cystic fibrosis sputum plus gelsolin; 1C: Cystic fibrosis sputum plus gelsolin amino acid fragment 1–260.

FIG. 2. Shear creep and recovery of cystic fibrosis sputum. Sputum samples with or without gelsolin or gelsolin fragment in between plates of the torsion pendulum were subjected to a constant shear stress. The subsequent deformation is quantified as the shear compliance, the ratio of shear strain to the imposed stress. Previous studies have shown that the compliance of F-actin increases sharply as the average filament length decreases (Janmey et al., *Biochemistry* 27:8218–8226 (1988)). The abrupt decreases in strain represent release of the applied stress.

DETAILED DESCRIPTION OF THE PREFERRED EMBODIMENTS

The present invention is based on the consideration that airway (respiratory tract) contents may contain actin filaments and DNA polymers which increase the consistency or viscosity of the airway contents and, by doing so, prevent normal clearance and lead to pathological consequences. Accordingly, an object of the invention is to reduce the consistency of pathological airway contents by causing the disaggregation or depolymerization of actin filaments, the inhibition of actin polymerization, reduction of actin levels, and the degradation of DNA polymers. Accordingly, in one embodiment of the invention, an actin-binding compound or compounds is introduced into the respiratory tract of a subject whose airway contents contain actin filaments and DNA polymers that contribute to respiratory distress. The actin-binding compound may disaggregate actin, prevent or reduce the polymerization of free monomeric actin, or prevent the binding of actin filaments or monomers to DNase I, or both. A general embodiment of the invention is a method for the solubilization or reduction in consistency or viscosity of pathological respiratory contents in the respiratory tract of individuals experiencing respiratory distress as a result of the presence of such contents.

The present invention is further based upon the consideration that airway mucus may contain actin filaments and DNA polymers which increase the consistency or viscosity of this mucus and thus prevent normal airflow and clearance. Accordingly, it is an object of the present invention to reduce the viscosity or consistency of such mucus by the administration, into the respiratory tract containing such mucus, of an actin-binding compound or compounds. The compound may act by disaggregating (depolymerizing) actin filaments into actin monomers, by binding to actin so as to prevent the binding of actin to DNase I, or both. The compound may also act by preventing the polymerization of actin monomers into filaments. By promoting mucus o clearance, the compound ultimately can reduce the levels of actin in the airway contents. Accordingly, in one embodiment of the invention, a method is provided for reducing the consistency or viscosity of airway mucus or solubilizing said mucus, by the introduction of an actin-binding compound or compounds into the respiratory tract of an individual whose respiratory tract contains said mucus.

The present invention is further based upon the consideration that purulent mucus in the respiratory tract contains significant leukocyte contamination such that said mucus contains DNA polymers increasing the consistency or viscosity of said mucus and may contain amounts of actin filaments such that the mucus contributes to airway obstruction, reduced expectoration, and other forms of respiratory distress. Accordingly, it is an object of the invention to reduce the consistency of purulent mucus by causing the disaggregation (depolymerization) of actin filaments that may be present in said mucus and by enhancing the degradation of DNA polymers present in said mucus. Therefore, in a preferred embodiment of the invention, the consistency or viscosity of purulent mucus is reduced by introducing into the respiratory tract of an individual with said mucus, an actin-binding compound or compounds. The actin-binding compounds may produce their effect by depolymerizing actin into actin monomers, binding to actin filaments and monomers so as to prevent their binding to DNase I, or both. The compound may also act by preventing the polymerization of actin monomers into filaments. By promoting mucus clearance, the compound ultimately can reduce the levels of actin in the airway contents.

In all embodiments of the invention, if DNase I is present, it can be either endogenous or added exogenously for therapeutic purposes. When it is added for therapeutic purposes, it may be co-administered with the actinbinding compound or separately.

In further embodiments of the invention, biologically active derivatives of the actin-binding compounds are administered to subjects with pathological airway contents, mucus, or purulent mucus in their respiratory tracts to protect against obstruction of the respiratory tract or reduction of expectoration.

In all embodiments of the invention, the methods are directed to reducing the consistency of the specific airway contents by instillation into the respiratory tract of a subject in need of such treatment, actin-binding compounds which may do one or more of the following: (1) disaggregate, depolymerize, fragment, and dissociate actin filaments released from disrupted leukocytes and other cells that solidify airway contents (2) prevent actin from inhibiting the action of DNase I which degrades DNA polymers by blocking actin binding to DNase I (3) ultimately reduce the level of actin in airway contents by promoting clearance of the contents. It is to be understood that the actin present in respiratory contents, for the purpose of the invention, is extracellular actin in said contents in free monomer or filament form.

In all embodiments of the invention in which the efficiency of DNase I is enhanced, the ultimate object of the embodiment is to enhance DNA degradation in pathological airway contents, and particularly in mucus and purulent mucus.

The diseases that are amenable to treatment by the methods of the present invention include, but are not limited to cystic fibrosis, chronic bronchitis, mucopurulent or purulent exacerbation of simple mucoid bronchitis, bronchorrhea, bronchopneumonia, widespread bronchiolitis, purulent pneumonia, pneumonic-alveolar-consolidation, asthma, with or without asthmatic bronchitis with mucus plugging, acute and/or chronic purulent sinusitis, empyema, bronchiectasis, bronchocoele, adult respiratory distress syndrome (ARDS), post-transplantation obliterative bronchiolitis, and allergenic bronchiolitis (fibrosing alveolitus).

In a preferred embodiment of the invention, the methods are practiced with the protein gelsolin or an active fragment thereof. Gelsolin may be instilled into the respiratory tract by routine methods such as those used to administer DNase I to subjects with respiratory distress. The treatment is not, however, limited to gelsolin.

In a further embodiment, additional gelsolin can be introduced into the airway by the intravenous route. The embodiment is based on the consideration that drug delivery by inhalation may be inherently limited in congested airways because of obstruction. Effective solubilization could be expected to enhance drug delivery by inhalation. On the other hand, an assault from the blood side may deliver the drug into alveoli as well as bronchioles and bronchi, such delivery being heightened by chronic inflammation and concomitant increased blood-tissue permeability.

It is known that plasma proteins can enter the airways as evidenced by α-1-antitrypsin therapy of hereditary emphysema. Presumably efficiency of blood to tissue delivery is a direct function of blood levels. Gelsolin levels can be measured to determine if airway binding to actin has had a depleting effect.

Since the major source of plasma gelsolin is muscle, it may be that levels fall as patients become increasingly cachectic in response to chronic infection and hypoxia.

It was shown (*Am. J. Path.* 130:261–267 (1988) and *Am. Rev. Resp. Dis.* 138:429–434 (1988)) that plasma gelsolin levels are depressed in experimental lung injury and in clinical ARDS, and others have claimed that there is some relationship between muscle mass and plasma gelsolin concentrations (Yamamoto, H., *Osaka Gas Group Foundation Publication* Volume 5:145–147 (1992)).

In order to provide a clearer and consistent understanding of the specification and claims, including the scope to be given such terms, the following definitions are provided.

The term "respiratory tract" or "airway" would be understood by the skilled artisan to refer to the tubular and cavernous organs and structures by means of which pulmonary ventilation and gas exchange between ambient air and blood are brought about. This would be understood to include, inter alia, the nasal cavity and conchae, the pharyngeal opening of the auditory tube, the pharynx, the larynx, the trachea, the bronchi, and the lungs. The invention is directed to treatment of airway contents, mucus, purulent mucus, etc. in any of the parts of the tract, particularly sub-tracheal.

It would be understood by the ordinary skilled artisan that "airway contents" or "respiratory tract contents" comprise a mixture of substances normally produced by the cells lining the airway (for example, through secretion) or remnants of the cells themselves. Accordingly, the skilled artisan would understand the term "pathological (mucoid) airway contents" or "pathological (mucoid) contents of the respiratory tract" to refer to those contents that contain components leading to structural and functional changes in the airway contents which cause abnormal respiratory tract function and/or disease. These include, but are not limited to, mucus, purulent mucus, thick mucus, such as in cystic fibrosis, bacteria, and the like. The components may also be biological components of mucus that alter the properties of mucus and cause disease or distress. The components themselves may be caused by an underlying disease state that contributes to an increase in the amount of normal airway contents or a change in the type of components from the components normally found in airway contents. For example, there may be an imbalance or disproportionate amount of certain components normally found in airway contents. By "respiratory distress" is meant the consequences of pathological airway contents which include, but are not limited to, reduced airflow, obstruction of the airway, reduced respiratory clearance by cilia, reduced respiratory clearance by muscular mechanisms such as coughing, clearing the throat, and sneezing, respiratory irritation from prolonged contact with the contents, the retention of leukocyte-derived lytic enzymes, inflammatory mediators, fungi, mycoplasma, bacteria, or other microorganisms.

By the term "mucus", the ordinary skilled artisan would understand the free slime of the mucus membranes, composed of secretion of the glands, along with various inorganic salts, desquamated cells, and leukocytes.

By the term "purulent mucus", for the purpose of the present invention, the skilled artisan would understand mucus that is rendered highly viscous, relatively solidified by DNA polymers derived from white blood cells and/or desquamated and/or broken endogenous airway cells.

The phrases "solubilizing (mucoid) airway contents", "solubilizing mucus", or "solubilizing purulent mucus" are intended to mean changing the mechanical properties of said contents, mucus, or purulent mucus so as to render such contents more like a liquid and less like a solid, more compliant, and better able to flow in response to shear stress. Disaggregation of polymers contributing to the viscosity of these components can also release proteins and other molecules trapped in the interstices of the contents/mucus/purulent mucus gel. The terms "reducing the viscosity" or "reducing the consistency" would also be understood to mean changing the mechanical properties, as described immediately above. The term "viscosity" would be understood by the skilled artisan to denote a physical property of a substance that is dependent on the friction of its component molecules as they slide by one another. A highly viscous solution would be characterized by a high degree of friction between component molecules, whereas a reduced viscosity would be characterized by a decrease in the degree of friction between component molecules as they slide by each other.

By "exogenous DNase" is intended DNase which is added by clinical means to a subject in need of such DNase by virtue of respiratory distress caused by DNA polymers in the subject's respiratory tract.

By "endogenous DNase" is intended DNase which is found in the respiratory tract of a subject, and particularly in the mucus of said subject's respiratory tract.

By the term "enhance DNA degradation" for the purposes of the present invention is intended adding that amount of an actin-binding compound which will bind to actin present in pathological airway contents, mucus, or purulent mucus, which actin, if not exposed to said actin-binding compound, would bind to DNase present in these fluids, inhibiting this DNase from reducing the amount of DNA polymer to allow decreased viscosity, enhanced respiratory airflow, expectoration, and relief from other forms of respiratory distress caused by the airway contents.

Actin-binding compound. "Actin-binding compound" is meant to include any compound, and especially any protein (or peptide), which is capable of binding actin so as to modify any of actin's many functions, including suppressing the ability of actin monomers to polymerize into filaments, to fragment (dissaggregate, depolymerize) pre-existing filaments, and to bind to DNase I. When administered to a subject in need of treatment, the actin-binding compounds of the invention are substantially free of natural contaminants which associate with such compound either in vivo (in a prokaryotic or eukaryotic host, or in vitro (as a result of a chemical synthesis). Such compounds include, but are not limited to extracellular actinbinding proteins such as gelsolin and DBP, and intracellular actin-binding proteins such as those most abundant in cells (for example, myosins, tropomyosins, profilin and cofilin) and those most abundant in non-muscle cells. Actin-binding compounds within the scope of the methods of the invention also include but are not limited to a) actin-binding compounds that predominantly sequester actin monomers, that is, bind monomers in a complex which is resistant to polymerization (for example, DBP, profilin, $\beta_4$-thymosin 1, cofilin, and DNase I); b) actin-binding compounds which sequester monomers and possess filament severing activity (for example, gelsolin, villin, fragmin and severin; c) actin-binding compounds that predominantly block the ends of actin filaments and prevent the exchange of monomers with that end (for example, tropomodulin, capZ, cap 100, ASP-56); and d) actin-binding nonproteinaceous molecules that have such effects on actin (for example, cytochalasin or biologically-active derivatives thereof, that block the ends of actin filaments and which are modified to remain extracellular). The skilled artisan would understand that useful compounds would remain extracellular in order to prevent any toxicity by interaction with functional intracellular actin. Fragments of actin-binding proteins with retained actin filaments-severing and/or monomer-sequestering activity are also within the scope of the present invention.

If desired, such compounds may be administered in the form of a pharmaceutically acceptable salt to the animal.

Animal. The term "animal" is meant to include all animals in which free actin or actin filaments in the sputum would be detrimental to the physiology of the animal. Foremost among such animals are humans; however, the invention is not intended to be so limiting, it being within the contemplation of the present invention to treat any and all animals which may experience the beneficial effect of the invention.

Efficacious Amount. An "efficacious amount" of an actin-binding compound is one which is sufficient to reduce or eliminate the toxic effects of actin in the respiratory tract contents of an animal. With respect to the present invention, it is the amount of compound effective to solubilize or reduce the viscosity or consistency of pathological airway contents, mucus, or purulent mucus, inhibit actin-binding to DNase I in these liquids or gels, enhance DNA degradation in these liquids or gels, or reduce the consistency of these liquids or gels so as to treat various forms of respiratory distress. An efficacious amount of an actin-binding compound is also that amount which may reduce bacterial content, the incidence of clinical infection, reduce the content of inflammatory mediators, or the content of degradative and cytotoxic enzymes in respiratory distress syndromes causing or caused by these liquids or gels.

The amount of the actin-binding molecule to be given, and the duration of therapy, may be determined by monitoring the frequency of exacerbation of symptoms or the deterioration of symptoms, the sputum volume and consistency, the pulmonary functions such as FEV, blood $pO_2$, pH, $pCO_2$, total lung capacity, residual volume tests of air flow, infection rate, etc. The skilled clinician would be familiar with routine monitoring techniques for respiratory treatment.

The amount of aerosolized actin binding protein may be determined according to those procedures used to determine the doses of DNase inhalation effective for treatment of patients with DNase I. For example, see Aitken, M. L., et al., *J. Am. Med. Assoc.* 267:1947–1951 (1992), particularly page 1948, "Study Design." The dose delivered in vivo is related to the effective amount determined in vitro. For example, if sputum is successfully solubilized in vitro by the amounts exemplified herein (i.e., 2–10 µg/ml), a thousand-fold increase over the in vitro dose would be administered (i.e., 2–10 mg/ml). Of course, it would be understood that the amounts and regimens for the administration of actin-binding compounds can be determined readily by those of ordinary skill in the art of treating respiratory disorders. Generally, the dosage of actin-binding compound treatment will vary depending upon considerations such as the type of the actin-binding compound employed, the age of the subject, the health of the subject, the severity of the disease, the kind of concurrent treatment, the extent of tissue damage, the gender of the patient, the duration of the symptoms, counterindications (if any), and other variables understood as needing adjustment by the individual physician. The correct effective dose could routinely be determined by monitoring the airway contents by aspiration or as sputum.

Substantially Free of Natural Contaminants. A material is said to be "substantially free of natural contaminants" if it has been substantially purified from materials with which it is normally and naturally found before such purification. Examples of natural contaminants with which actin-binding compounds might be associated are: non-actin-binding peptides, carbohydrates, glycosylated peptides, lipids, membranes, etc. A material is said to be substantially free of natural contaminants if those contaminants normally and naturally found with the substance in vivo or in vitro are substantially absent from a sample of the material. By "substantially absent" is meant that such contaminants are either completely absent or are present at such low concentrations that their presence (1) does not interfere with the desired therapeutic effect of the active agent (herein the actin-binding compound) in the preparation when such preparation is administered to an animal and (2) does not harm the animal as the result of the administration of such preparation.

Administration. The term "administration" is meant to include introduction of actin-binding compounds into the respiratory tract of an animal by any appropriate means known to the medical art, including, but not limited to inhalation of an aerosolized compound, installation by bronchoscopy, and intravenous infusion.

The actin-binding compounds of the present invention may be co-administered with DNase or one actin-binding compound may be co-administered with one or more distinct actin-binding compounds. By the term "co-administer" is intended that each of at least two compounds be administered during the time frame wherein the respective periods of biological activity overlap. Thus, the term includes sequential as well as coextensive administration of the compounds of the present invention with each other or with DNase I.

Pharmaceutically Acceptable Salt. The term "pharmaceutically acceptable salt" is intended to include salts of the actin-binding compounds of the invention. Such salts can be formed from pharmaceutically acceptable acids or bases, such as, for example, acids such as sulfuric, hydrochloric, nitric, phosphoric, etc., or bases such as alkali or alkaline earth metal hydroxides, ammonium hydroxides, alkyl ammonium hydroxides, etc.

Pharmaceutically Acceptable Vehicle. The term "pharmaceutically acceptable vehicle" is intended to include solvents, carriers, diluents, and the like, which are utilized as additives to preparations of the actin-binding compounds of the invention so as to provide a carrier or adjuvant for the administration of such compounds.

Treatment. The term "treatment" or "treating" is intended to include the administration of actin-binding compounds to a subject for purposes which may include prophylaxis, amelioration, prevention or cure.

Fragment. The term "fragment" is meant to include any portion of a molecule which provides a segment of an actin-binding compound which is capable of binding actin monomers and/or severing filaments; the term is meant to include actin-binding fragments which are made from any source, such as, for example, from naturally-occurring peptide sequences, synthetic or chemically-synthesized peptide sequences, and genetically engineered peptide sequences. Further, if such fragment is a peptide, a fragment of a peptide of such actin-binding protein is meant to include to any variant of the actin-binding protein.

Variant. A "variant" is meant to refer to a compound substantially similar in structure and biological activity to either the native compound, or to a fragment thereof.

The biological activity of the compounds of the invention is their ability to bind actin and modify it into a form which is less toxic to an animal than unmodified actin. Such modification may be the result of the binding of the compounds per se or the result of a chemical or enzymatic reaction which results from such binding.

Functional Derivative. A "functional derivative" of an actin-binding compound is a derivative which possesses a biological activity that is substantially similar to the biological activity of the actin-binding compound. By "substantially similar" is meant activity which is quantitatively different but qualitatively the same. For example, a functional derivative of an actin-binding protein of the invention would contain the same amino acid backbone as an actin-binding protein but also contains other modifications such as post-translational modifications such as, for example, bound phospholipids, or covalently linked carbohydrate, depending on the necessity of such modifications for the performance of the diagnostic assay or therapeutic treatment. As used herein, the term is also meant to include a chemical derivative of an actin-binding compound. Such derivatives may improve the compound's solubility, absorption, biological half life, etc. The derivatives may also decrease the toxicity of the molecule, or eliminate or attenuate any undesirable side effect of the molecule, etc. Derivatives and specifically, chemical moieties capable of mediating such effects are disclosed in *Remington's Pharmaceutical Sciences* (1980). Procedures for coupling such moieties to a molecule are well known in the art. The term "functional derivative" is intended to include the "fragments," "variants," "analogues," or "chemical derivatives" of a molecule.

Analog. An "analog" of the actin-binding compounds of the invention is meant to refer to a compounds substantially similar in function to either the native actin-binding compound or to a fragment thereof. For example, an analog of an actin-binding protein is a protein which does not have the same amino acid sequence as an actin-binding protein but which is sufficiently homologous to an actin-binding protein so as to retain the biological activity of such actin-binding protein.

The particular actin-binding molecules that are the subject of the methods of the invention are purified native and recombinant actin-binding proteins, and other non-proteinaceous actin-binding molecules, and biologically-active fragments thereof, which are characterized by the presence of unique actin binding domains which possess the biological activity of being able to sequester actin in a monomeric form or rapidly to disaggregate or depolymerize actin filaments or to cover sites on free actin that are toxic to host cells. Individual actin-binding domains possessing this biological activity may also be produced by synthetic, enzymatic, proteolytic, chemical or recombinant DNA methods.

In a preferred embodiment, gelsolin, DBP, or actin-binding fragments thereof, or, a combination of gelsolin and DBP and/or actin-binding fragments thereof, are provided to the subject in need of treatment. Other actin-binding proteins reasonably expected to be effective for the purposes of the invention include $\beta_4$ thymosin and ASP-56.

Preparations of the actin-binding proteins of the invention for parenteral administration include sterile aqueous or non-aqueous solvents, suspensions and emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles include fluid and nutrient replenishers, electrolyte replenishers, such as those based upon Ringer's dextrose and the like.

The actin-binding proteins of the invention may also be administered by means of pumps, or in sustained-release form, especially, when the primary injury is prolonged or delayed rather an acute.

Administration in a sustained-release form is more convenient for the patient when repeated injections for prolonged periods of time are indicated. For example, it is desirable to administer the actin-binding proteins of the invention in a sustained-release form when the methods of the invention are being used to treat a genetic or chronic disease based upon an actin-related disorder so as to maximize the comfort of the patient.

The actin-binding proteins of the invention can be employed in dosage forms such as tablets, capsules, powder packets, or liquid solutions for oral administration if the biological activity of the protein is not destroyed by the digestive process and if the characteristics of the compound allow it to be absorbed across the intestinal tissue.

The pharmaceutical compositions of the present invention are manufactured in a manner which is in itself know, for example, by means of conventional mixing, granulating, dragee-making, dissolving, lyophilizing or similar processes. The compositions of the present invention, in and of themselves, find utility in the control of actin-induced physiological damage, be it chronic or acute. The compositions of the invention direct the body's own mechanisms for dealing with excess actin in the bloodstream or extracellular tissues to its maximum potential. In intravenous dosage form, the compositions of the present invention have a sufficiently rapid onset of action to be useful in the acute management of potential tissue damage.

Actin-binding proteins which are substantially free of natural contaminants can be isolated and purified from their natural or recombinant sources in accordance with conventional conditions and techniques in the art previously used to isolate such proteins, such as extraction, precipitation, chromatography, affinity chromatography, electrophoresis, or the like.

One of skill in the art can identify the actin-binding domain(s) of an actin-binding compound using techniques known in the art, without undue experimentation, and such domains are preferred in the methods of the invention. For example, derivatives of the native actin-binding proteins, or, derivatives of recombinantly produced actin-binding proteins, can be made by proteolytic cleavage of the full-length actin-binding protein with common proteases, such as, for example, trypsin, chymotrypsin, and subtilisin. Affinity chromatography with actin-derivatized resins may be used to assay such fragments for their actin-binding ability.

When identification of compounds or fragments thereof which possess actin-severing activity is desired, such compounds or fragments can also be identified using techniques known in the art, for example, by following the rate of depolymerization of pyrene-labeled F-actin.

Further, such fragments may be identified by their homology to other known actin-binding or actin-severing domains wherein it may be predicted that function will follow homology. For example, it is known that severin, gelsolin and villin, and especially amino acid residues 40-35 1 in severin and amino acid residues 63-383 in gelsolin, show extensive homology in the domain responsible for F-actin severing activity.

The N-terminal half of gelsolin, for example, an N-terminal tryptic fragment known as CT45, is capable of severing F-actin and contains two actin binding sites. Efficacious amounts of CT45 which are substantially free of natural contaminants can be administered to a patient. One of these sites resides in a chymotryptic fragment, CT15N (human gelsolin residues 24-150), which binds the ends of actin monomers and filaments with high affinity; the other site is contained in the adjacent fragment CT28N (residues 151-406), which binds to the side of F-actin in a polyphosphoinositide-regulated manner. Neither of the fragments sever actin filaments by themselves. The smallest gelsolin polypeptide which is capable of severing F-actin encompasses residues 5-165 of plasma gelsolin.

Further, compounds such as actin-binding proteins are highly conserved among species and can be easily isolated in large quantities from nonhuman (bovine, porcine) plasma and/or muscle tissues and fragments of these proteins can be chemically or enzymatically prepared by techniques well-known in the art. Thus such actin-binding compounds can be administered to a subject in need of the therapeutic methods of the invention without provoking a severe immune response.

All references cited in this application are incorporated herein by reference. Having now generally described the invention, the following examples further describe the materials and methods used in carrying out the invention. The examples are not intended to limit the invention in any manner.

EXAMPLES

Example 1

Specimens of expectorated sputum from patients with cystic fibrosis, some of whom had received aerosolized DNase I, were thawed and separated into sections. The procedure described by Shak et al. (*Proc. Natl. Acad. Sci. USA* 87:9188–9192 (1990)) for determining the effect of DNase I on sputum consistency was followed, except that instead of adding DNase I, purified plasma gelsolin was added. This protein non-covalently severs actin polymers. A recombinant gelsolin fragment produced in E. coli and encompassing amino acid residues 1-260 of gelsolin ("gelsolin 260"), capable also of fragmenting actin filaments, was also used. These proteins, which have no known effects on DNA, essentially gave the same results described by Shak et al., (*Proc. Natl. Acad. Sci. USA* 87:9188–9192 (1990)) in the pourability test for cystic fibrosis sputum. The gelsolin fragment was more effective than gelsolin, although it was added at a three-fold higher concentration (Table 1).

TABLE 1

Sputum samples of about 150 mg were divided by cutting with a razor blade and placed in test tubes containing the indicated additives in 50 mL volumes. Samples were incubated at 37° C. in test tubes which were inverted at the time intervals shown in the table, and the presence and extent of movement noted of sputum following a tap on the side of the tube; 0 = no movement; Tr = <10% of the sputum moved down the side of the inverted tube; 1+ = 10–20% of the sputum moved; 2+ = 20–50% of the sputum moved, 3+ = >50% of the sputum moved; 4+ = all of the sputum moved.

| Additive | 0 min | 15 min | 30 min | 60 min |
|---|---|---|---|---|
| 0.15M NaCl | 0 | Tr | Tr | Tr |
| +0.5 mM gelsolin | 0 | 2+ | 3+ | 4+ |
| +5 mM gelsolin fragment | 0 | 3+ | 4+ | 4+ |

The experiments were repeated with additional samples of sputum, and gave identical results. Boiled gelsolin fragment was inactive.

Example 2

Figure 1A:
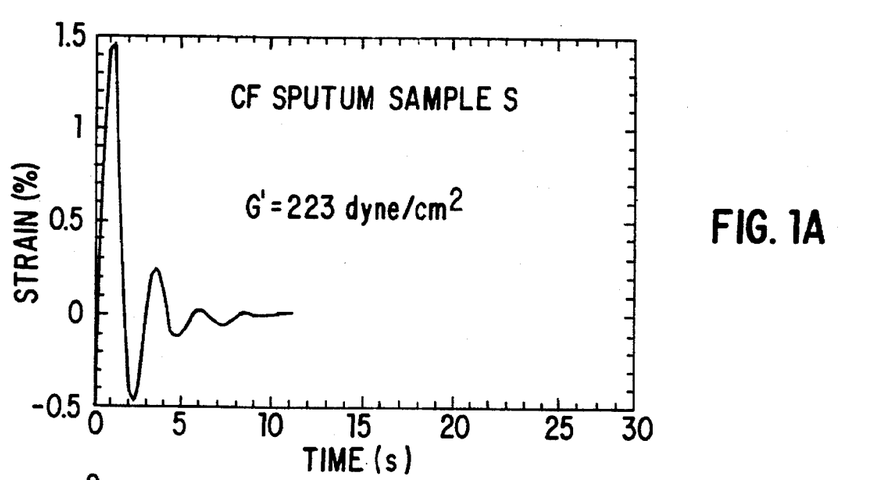
Figure 1B:
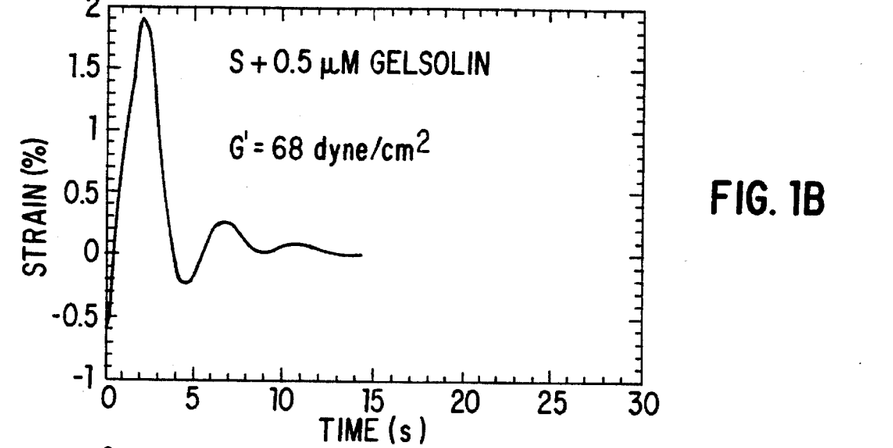
Figure 1C:
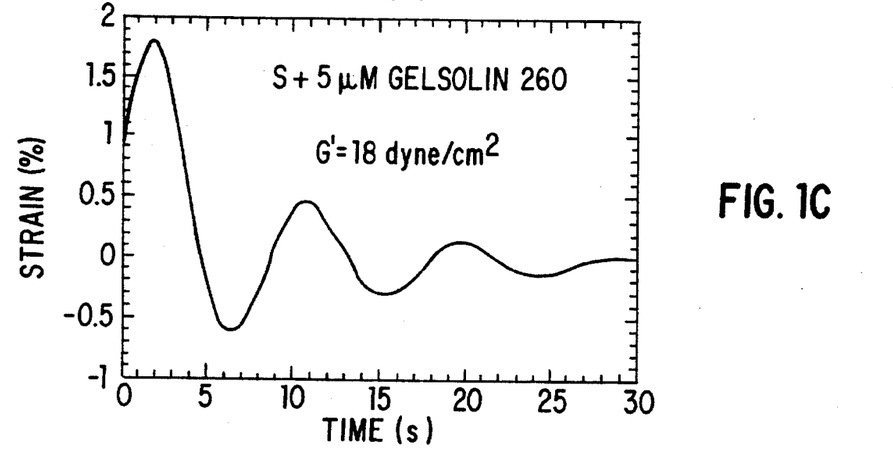
Figure 2:
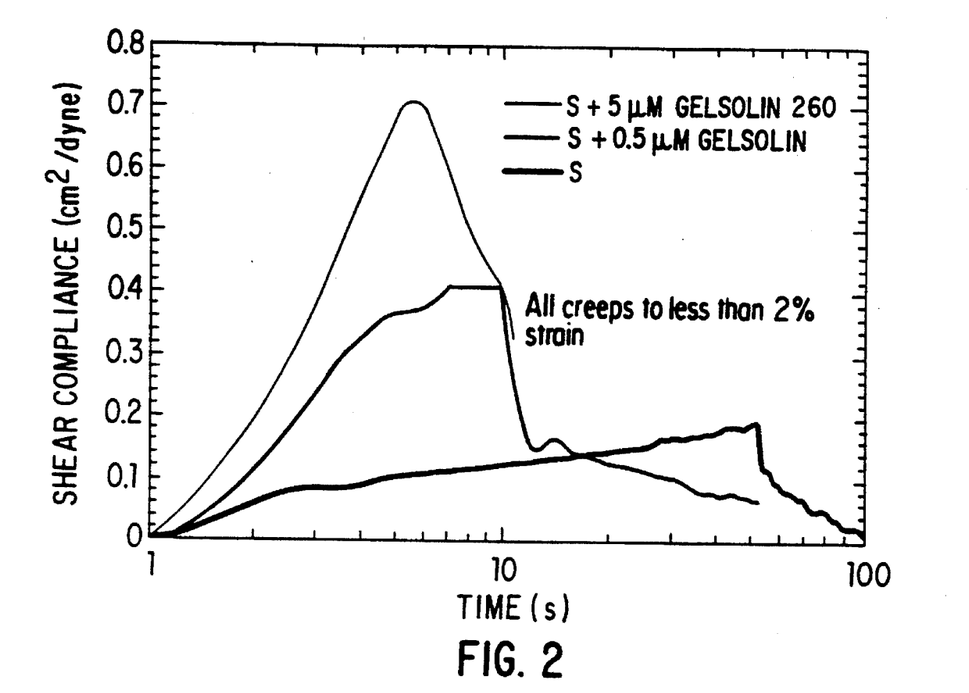

Sputum samples were studied with a more formal rheological assay involving a torsion pendulum. As shown in FIG. 1A, cystic fibrosis sputum was very rigid and elastic, as indicated by the high frequency oscillations induced by a transient stress, from which an elastic modulus (G') of could be calculated. Addition of gelsolin (1B) and gelsolin fragment (1C) reduced the frequency of the oscillations, lowering the moduli 3- and 10-fold respectively. Again, the fragment, present in higher concentration, was more effective than gelsolin. The strain response (known as "creep") of sputum to a steady stress showed the inherent stiffness or poor compliance of cystic fibrosis sputum, whereas gelsolin and gelsolin fragment, again in a dose-response manner, increased the creep compliance. All samples, however, recovered their original positions following the removal of the stress, indicating that coherent polymers, possibly mucopolysaccharides and DNA, remained in the gels.

Example 3

Rhodamine phalloidin, which binds to polymeric actin, was added to cystic fibrosis sputum specimens which were then observed in the phase contrast and fluorescence microscopes. The samples contained cellular debris, the presumed source of DNA and actin, and were brightly fluorescent. Untreated and gelsolin-fragment-treated sputum plugs were diluted in 2.5 ml of 0.15M NaCl solution and centrifuged. The absorbance at 280 nm was determined as an indication of how much protein was released from the sputum gels. The results are shown in Table 2 and show that gelsolin and the 260 kDa fragment released protein from the sputum plugs.

TABLE 2

| Sample | OD @ 1 = 280 nm (OD) |
|---|---|
| Sputum alone | 0.015 |
| Sputum + 1.5 mM gelsolin | 0.249 |
| Sputum + 2.1 mM 260 fragment | 0.247 |

Analysis of protein released from cystic fibrosis sputum gels incubated with gelsolin. Samples of 50 µl from the supernatant solutions on which the optical densities had been determined were added to an equal volume of sodium dodecyl sulfate- and β-mercaptoethanol-containing buffer solution, and polypeptides in this mixture were resolved by polyacrylamide gel electrophoresis. The gel was stained with Coomassie blue. The gel showed that the gelsolin- and gelsolin fragment-containing solutions contained many different proteins and large amounts of three proteins, including one co-migrating with actin used as a molecular weight standard, than with the control supernatant.

Anti-actin antibody immunoblot study of cystic fibrosis sputum. Duplicates of cystic fibrosis sputum from two different patients were suspended in an equal volume of 0.15M sodium chloride 20 mM Tris-HCl, pH 7.0, and homogenized. 50 µL of the material was added to an equal volume of SDS gel buffer and resolved by electrophoresis on a polyacrylamide gel. The gel polypeptides were transferred to nitrocellulose and the actin band identified with an anti-actin antibody. Bands were seen in the lanes containing the sputum. This result confirms that actin is present in cystic fibrosis sputum.

Example 4

Solubilization of Purulent Sputum by Actin-Binding Proteins. Samples of fresh sputum from CF patients were obtained and tested within a few hours of collection. In this test, commercial bovine DNase I was compared directly with purified plasma gelsolin in the pourability assay (Table 3):

TABLE 3

| Time of incubation at 37° C. | Gelsolin | | | DNase I | | |
|---|---|---|---|---|---|---|
| | Concentration, µg/ml | | | | | |
| | 2 | 5 | 10 | 2 | 5 | 10 |
| 1 min | 0 | 0 | 3+ | 0 | 0 | 0 |
| 3 min | 0 | Tr | 3+ | 0 | 0 | Tr |
| 5 min | Tr | 2+ | 4+ | Tr | Tr | Tr |
| 10 min | Tr | 2+ | 4+ | Tr | Tr | 2+ |
| 15 min | Tr | 2+ | 4+ | Tr | 1+ | 3+ |

Since the molecular weight of DNase I is 31,000 and that of gelsolin, 84,000, gelsolin is considerably more effective on a weight basis. Also, the rapid onset of action is consistent with a stoichiometric action expected for gelsolin, whereas the slower onset for DNase is more consistent with depolymerization by end loss of monomers rather than fragmentation of actin polymers or enzymatic action on DNA.

Example 5

Synergy between DNase I and gelsolin; Concentration-dependent release of proteins. A protein release experiment was done that showed concentration-dependent dissolution of sputum samples from three cystic fibrosis patients. Sputum samples of about equivalent volume were suspended in 0.5 ml of a 0.15M NaCl solution containing purified plasma gelsolin concentrations of approximately 2.0 µg/ml, 4 µg/ml, 7 µg/ml, and 21 µg/ml. After incubation at 37° C. for 30 minutes, the samples were centrifuged and the optical density ($\gamma$=280 nm) of the supernatant solutions were determined. On a relative scale, the $A_{280}$ readings were as follows: 2 µg/ml: 0.25; 4 µg/ml: 1.30; 7 µg/ml: 1.86; 21 µg/ml: 180. The $A_{280}$ after 4 µg/ml DNase I was approximately 0.5. The $A_{280}$ after 4 µg/ml DNase I plus 2 µg/ml gelsolin was approximately 1.3. Gelsolin produced more dissolution expected at a low dose in the presence of a basally ineffective DNase I concentration.

Now having fully described this invention, it will be understood by those with skill in the art that the scope may be performed within a wide and equivalent range of condition, parameters, and the like, without affecting the spirit or scope of the invention or of any embodiment thereof.

What is claimed is:

1. A method for solubilizing mucus in the respiratory tract of a subject comprising the step of administering an efficacious level of at least one actin-binding compound, other than DNase I, into the respiratory tract of said subject wherein said actin-binding compound sequesters actin monomers, severs actin filaments, or prevents or reduces the polymerization of actin.

2. The method according to claim 1, wherein DNase I is co-administered to said subject.

3. A method for reducing the viscosity of mucus in the respiratory tract of a subject comprising the step of administering an efficacious level of at least one actin-binding compound, other than DNase I, to said subject wherein said actin-binding compound sequesters actin monomers, severs actin filaments, or prevents or reduces the polymerization of actin.

4. The method according to claim 3, wherein DNase I is co-administered to said subject.

5. A method of treating respiratory tract obstruction in a subject, wherein said obstruction is caused by the presence of mucus in the respiratory tract of said subject, comprising the step of administering an efficacious level of at least one actin-binding compound, other than DNAse I, to said subject wherein said actin-binding compound sequesters actin monomers, severs actin filaments, or prevents or reduces the polymerization of actin.

6. The method according to claim 5, wherein DNase I is co-administered to said subject.

7. The method according to any one of claims 1–6, wherein said actin-binding compound is gelsolin or an active fragment thereof.

8. The method according to claim 7, wherein said active fragment is the chymotryptic fragment CT45.

9. The method according to claim 7, wherein said active fragment contains amino acid residues 25–165 of gelsolin.

10. The method according to any one of claims 1–6, wherein said actin-binding compound is DBP.

11. The method according to any one of claims 1–6, wherein said mucus is associated with a pathological respiratory condition selected from the group consisting of cystic fibrosis, chronic bronchitis, mucopurulent or purulent exacerbation of simple mucoid bronchitis, bronchopneumonia, widespread bronchiolitis, asthma, asthma with asthmatic bronchitis with mucus plugging, acute purulent sinusitis, chronic purulent sinusitis, bronchiectasis, bronchocoele, post-transplantation obliterative bronchiolitis, and allergenic bronchiolitis (fibrosing alveolitus).

12. The method according to any one of claims 1–6, wherein said actin-binding compound possesses filament-severing activity.

13. The method according to claim 12, wherein said actin-binding compound is selected from the group consisting of gelsolin, villin, fragmin and severin.

14. The method according to any one of claims 1–6, wherein said actin-binding compound sequesters actin monomers in complexes that resist polymerization.

15. The method according to claim 14, wherein said actin-binding compound is selected from the group consisting of vitamin D binding protein, cofilin and profilin.

16. The method according to any one of claims 1–6, wherein one actin-binding compound is gelsolin or an active fragment thereof and another actin-binding compound is DBP.

* * * * *